(12) United States Patent
Krespan et al.

(10) Patent No.: US 6,262,320 B1
(45) Date of Patent: Jul. 17, 2001

(54) ADDITION OF TRIFLUOROMETHANES TO FLUOROOLEFINS AND ISOMERIZATION OF MONOHALOPERFLUORO ALKANES

(75) Inventors: Carl George Krespan, Wilmington; Viacheslav Alexandrovich Petrov, Hockessin, both of DE (US)

(73) Assignee: E. I. duPont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/516,593

(22) Filed: Mar. 29, 2000

Related U.S. Application Data

(62) Division of application No. 08/981,760, filed as application No. PCT/US96/10872 on Jun. 25, 1996.

(60) Provisional application No. 60/000,720, filed on Jun. 30, 1995.

(51) Int. Cl.$^7$ .................................................. C07C 19/08
(52) U.S. Cl. ................................................................ 570/151
(58) Field of Search ............................................... 570/151

(56) References Cited

U.S. PATENT DOCUMENTS 5,416,246 * 5/1995 Krespan et al. ..................... 570/151

* cited by examiner

*Primary Examiner*—Alan Siegel

(57) ABSTRACT

A process for the Lewis acid catalyzed addition of trifluoromethanes across the carbon-carbon double bond of fluoroolefins is disclosed. A process for isomerization of monohaloperfluoro alkanes is also disclosed.

9 Claims, No Drawings

ADDITION OF TRIFLUOROMETHANES TO FLUOROOLEFINS AND ISOMERIZATION OF MONOHALOPERFLUORO ALKANES

This is a division of application Ser. No. 08/981,760 filed Dec. 29, 1997, now pending that claims priority from PCT U.S. 96/10872 filed on Jun. 25, 1996 that claims priority from provisional Application No. 60/000,720 filed on Jun. 30, 1995.

FIELD OF THE INVENTION

This invention concerns a process for the Lewis acid catalyzed addition of trifluoromethanes across the carbon-carbon double bond of fluoroolefins.

TECHNICAL BACKGROUND

U.S. Pat. No. 5,157,171 discloses a process for the preparation of chlorofluoropropanes of the formula $C_3HCl_2F_5$ by contacting monofluorodichloromethane with tetrafluoroethylene in the presence of modified aluminum chloride catalyst.

U.S. Pat. No. 5,416,246 discloses the rearrangement of dichlorofluorocarbons to gem-dichloro chlorofluorocarbons in the presence of a mixed aluminum halide catalyst.

U.S. Pat. No. 2,462,402 discloses a process for the production of highly halogenated fluoroalkanes which comprises contacting TFE with a polyhalogenated alkane, preferably a methane, containing at least one chlorine atom and no more than two fluorine atoms, in the presence of a polyvalent metal halide catalyst, preferably aluminum chloride.

U.S. Pat. No. 2,462,402 is referred to in the Journal of the American Chemical Society, Vol. 71, pages 979–980 (1949) which discloses reacting $CHClF_2$ (chlorodifluoromethane) while in the presence of aluminum chloride with TFE produces $C_3HCl_2F_5$ having one less F atom than the sum of fluorine atoms in the reactants. Likewise, $CHClF_2$ reacting with CTFE yields $C_3HCl_3F_4$.

Paleta, in a review article "Fluorine Chemistry Reviews", Vol. 8, page 51 (1977) states: "The ionic addition reactions of fluoromethanes in the presence of aluminum chloride are limited to the monofluoro derivatives only. When in contact with aluminum chloride, both difluorodichloromethane and difluorochloromethane were found to undergo a rapid disproportionation with the formation of monofluorochloromethanes (along with some further compounds) that are able to add to fluoroethylenes".

The disclosure of each of the previously identified references is hereby incorporated by reference.

SUMMARY OF THE INVENTION

This invention provides a process for the addition of trifluoromethanes of the structure $CF_3X$, where X is I, Br, Cl, or H to olefins of the structure $YFC=CF_2$, where Y is H, F, Cl or $OC_nF_{2n}F$, where n is 1,2 or 3 in the presence of Lewis acid catalyst. The process is conducted optionally with agitation, and optionally in the presence of a solvent or diluent that is not reactive in the process. The process affords adducts of the structure $CF_3CFYCF_2X$, if Y is H, F or Cl or its isomer, $YCF_2CF_2CF_2X$, if Y is $OC_nF_{2n}F$, where n is 1,2 or 3. Products may further isomerize in the presence of a Lewis Acid catalyst. A preferred Lewis acid catalyst is aluminum chlorofluoride.

This invention further provides a process for the isomerization of $R_fCF_2CF_2X'$, where $R_f$ is $C_1-C_{12}$ and where X' is I or Br, to $R_fCFX'CF_3$, in the presence of a Lewis acid/fluoroolefin catalyst system. A preferred Lewis acid in the catalyst system is aluminum chlorofluoride. The fluoroolefin is $C_3$ to $C_{12}$ and may be cylic or linear.

DETAILED DESCRIPTION OF THE INVENTION

For the compound $CF_3X$, where X is selected from the group consisting of I, Br, Cl, and H, the preferred X's are I, Br or H.

In the olefin of the structure $YFC=CF_2$, it is preferred that Y is H or F.

Solvents or diluents may be employed in the process of the present invention. The solvent or diluent is selected so that it will not be reactive in the process or lead to the deactivation of the aluminum chlorofluoride catalyst. Suitable solvents or diluents are selected from the group consisting of perfluoroalkanes or perfluorocycloalkanes, for example, perfluorocyclobutane; the cyclic dimer of hexafluoropropene, i.e., the isomeric perfluorodimethylcyclobutanes; perfluoroethers; or perfluoro tertiary amines. Preferred on the basis of its ready availability to those skilled in the art is the cyclic dimer of hexafluoropropene.

The temperature employed in the process of the present invention ranges from about −10° C. to about 180° C. The preferred temperature range is about 0° C. to 150° C.

Reaction time is not critical and ranges from about several minutes to about 24 hours. About 1 to 16 hours, are usually sufficient.

The pressure employed in the reaction is not critical. Autogenous pressures are usually employed.

Where the reaction conditions are heterogeneous, some degree of agitation is often desirable.

The reaction is preferably carried out in the presence of an aluminum halide Lewis acid catalyst, wherein the aluminum halide is a mixed halide containing fluorine and at least one of Cl, Br or I. Preferred catalysts are of the structure $AlF_nCl_{3-n}$, wherein n is from 0.05 to 2.95. Preferably n is from 2.5 to 2.95. Fluorinated aluminum chloride catalysts can be prepared by the reaction of $AlCl_3$ with a fluoroalkane such as $CFCl_3$ according to the method described in U.S. Pat. No. 5,162,594, column 4, lines 35–57, which is hereby incorporated by reference. Catalysts may be preformed or may be generated in situ.

Since the catalyst is water sensitive, reagents and equipment should be dried before use.

The proportion of catalyst to $CF_3X$ is preferably about 0.05 to 0.20 mole catalyst per mole $CF_3X$.

The process is used to prepare useful chemical intermediates, for example, $CF_3CF_2CF_2I$ by the reaction of $CF_3I$ with $CF_2=CF_2$. This process offers a particularly straightforward and economical synthesis of this compound. Propyl iodide is useful as an intermediate for preparing higher fluoroalkyl iodides, for example by further reacting them with TFE or, after the elinination of HI from said perfluoroalkyl iodides, the preparation of perfluoroolefins.

Previous syntheses of this compound involved the expensive conversion $CF_3CF_2CF_2C(O)OAg + I_2 \rightarrow CF_3CF_2CF_2I$.

Primary halides including some of the products of the process of the present invention, i.e., $R_fCF_2CF_2X'$, where $R_f$ is $C_1-C_{12}$ and X' is I or Br, may be rearranged to isomers under some reaction conditions i.e., in the presence of Lewis acid catalyst, preferably aluminum chlorofluoride catalyst plus fluoroolefin co-catalyst, at appropriately high temperatures and residence times to compounds of the type $R_fCFX'CF_3$.

EXAMPLES

Catalyst Preparation—AlCl$_3$+CFCl$_3$ 500 g (3.75 mol) of AlCl$_3$ (Aldrich—99% pure) was stirred mechanically under N$_2$ in a r.b. flask fitted with a −80° C. condenser while 1750 mL (~2625 g, 19 mol) of CFCl$_3$ was added over a 1.5-hr period. Reaction is very exothermic in the early stages, so addition of CFCl$_3$ was slow at first in order to keep the temperature below 65° C., then rapid. The resulting suspension was stirred an additional 3 hrs while volatiles (CF$_2$Cl$_2$) were allowed to escape through the warmed condenser. The condenser was then replaced with a simple stillhead, and most of the CCl$_4$ was distilled under reduced pressure [mainly bp 38° C. (200 mm)]. Finally, the last traces of volatiles were removed by warming the residual solid to 30–35° C. at 0.05 mm.

The sealed r.b. flask was transferred to a dry box and unloaded into a Teflon® FEP bottle; 340 g of rather finely divided yellow-green solid. Portions of the catalyst were weighed out in the dry box as needed and taken out in plastic bottles with pressure-seal caps.

Analysis for fluorine of the products from preparation of this type indicated the composition to be AlF$_{2.9}$Cl$_{0.1}$, AlF$_x$Cl$_y$; X=2.8–2.9, Cl=0.2–0.1.

Example 1

Reaction of Trifluoromethyl Iodide with TFE

A 240 mL Hastelloy shaker tube was flushed with nitrogen, then loaded with 3 g of aluminum chlorofluoride catalyst, closed, cooled to −78° C., evacuated and loaded with 60 g (0.31 mole) of trifluoromethyl iodide and 15 g (0.15 mole) of tetrafluoroethylene. The reaction vessel was allowed to warm and kept on a shaker at 25–30° C. at autogenous pressure for 16 hours. After 16 hours, the pressure tube was unloaded. The excess trifluoromethyl iodide was distilled out of the crude product using a low temperature distillation column to give 28 g of recovered starting trifluoromethyl iodide. The residue was distilled to give 38 g of material with boiling point 35–40° C. According to gas chromatography and $^{19}$F NMR, this mixture contained 95% of perfluoro-n-propyl iodide and 5% of perfluoroisopropyl iodide. The calculated yield of both isomeric propyl iodides was 84.4%.

Example 2

Reaction of Trifluoromethyl Bromide with TFE

A 240 mL Hastelloy shaker tube was flushed with nitrogen, then loaded with 1 g of aluminum chlorofluoride catalyst and 50 mL of hexafluoropropene cyclodimer (dried over P$_2$O$_5$) as solvent, closed, cooled to −78° C., evacuated and loaded with 45 g (0.3 mole) of trifluoromethyl bromide and 35 g (0.35 mole) of tetrafluoroethylene. The reaction vessel was allowed to warm and kept on a shaker at 25–30° C. at autogenous pressure for 16 hours. After 16 hours, the pressure tube was unloaded and the contents were distilled. There were obtained 50.1 g of material of boiling point 12–13° C. According to $^{19}$F NMR, this product was a mixture containing 93% of perfluoro-n-propyl bromide, 6% of perfluoroisopropyl bromide and 1% residual solvent. The calculated yield of both isomeric propyl bromides was 67%.

Example 3

Reaction of Trifluoromethyl Chloride with TFE

A 240 mL Hastelloy shaker tube was flushed with nitrogen, then loaded with 2 g of aluminum chlorofluoride catalyst and 50 mL of hexafluoropropene cyclodimer (dried over phosphorous pentoxide, P$_2$O$_5$) as solvent, closed, cooled to −78° C., evacuated and loaded with 42 g (0.4 mole) of trifluoromethyl chloride and 30 g (0.3 mole) of tetrafluoroethylene. The reaction vessel was heated to 50° C. and kept on a shaker at 50° C. at autogenous pressure for 16 hours. After 16 hours, the pressure tube was unloaded and the contents were distilled. There were obtained 10 g of material of boiling point range −10° C.−+20° C. According to $^{19}$F NMR, this product was a mixture containing 30% of perfluoro-n-propyl chloride and 70% residual solvent. 22 g of polytetrafluoroethylene was also obtained. The calculated yield of perfluoro-n-propyl chloride was 4.2%. $^{19}$F NMR: CF$_3^A$CF$_2^B$CF$_2^C$Cl, A −80.62 (3F,t), B −125.30 (2F,s), C −69.83 (2F,q); J$_{A-C}$=8.7 Hz.

Example 4

Reaction of Trifluoromethane with TFE

A 240 mL Hastelloy shaker tube was flushed with nitrogen, then loaded with 2 g of aluminum chlorofluoride catalyst and 30 mL of hexafluoropropene cyclodimer (dried over P$_2$O$_5$) as solvent, closed, cooled to −78° C., evacuated and loaded with 21 g (0.3 mole) of trifluoromethane and 30 g (0.3 mole) of tetrafluoroethylene. The reaction vessel was heated to 50° C. and kept on a shaker at 50° C. at autogenous pressure for 16 hours. After 16 hours, the pressure tube was unloaded and the contents were distilled. There were obtained 14.6 g of material of boiling point range −17° C.−−10° C. (main −16° C.−−15° C.). According to $^{19}$F NMR, this product consisted of 1,1,2,2,3,3,3-heptafluoro-n-propane. 15 g of polytetrafluoroethylene was also obtained. The calculated yield of 1,1,2,2,3,3,3-heptafluoro-n-propane was 29.4%.

Example 5

Reaction of Trifluoromethane with Trifluoroethylene

A 240 mL Hastelloy shaker tube was flushed with nitrogen, then loaded with 3 g of aluminum chlorofluoride catalyst and 30 mL of hexafluoropropene cyclodimer (dried over P$_2$O$_5$) as solvent, closed, cooled to −78° C., evacuated and loaded with 28 g (0.4 mole) of trifluoromethane and 32 g (0.39 mole) of trifluoroethylene. The reaction vessel was heated to 25–30° C. and kept on a shaker at 25–30° C. at autogenous pressure for 16 hours. After 16 hours, the pressure tube was unloaded and the contents were distilled. There were obtained 2.1 of material of boiling point range −4° C.−−6° C. According to $^{19}$F NMR, this product consisted of 1,1,2,3,3,3-hexafluoro-n-propane. The calculated yield was 3%.

Example 6

Isomerization of N-perfluoropropyl Iodide

In a dry box, 0.5 g of aluminum chlorofluoride catalyst were placed in a heavy walled Pyrex® glass sample tube equipped with a Teflon® stopcock. The sample tube was evacuated at −196° C. and perfluoro-n-propyl iodide (98% pure from PCR Corp, Gainesville Fla.), 20 mmol, and 3 mmol of hexafluoropropene (HFP) were added through the vacuum line. The sample tube was kept at 25° C. for 12 hours. At that time, $^{19}$F NMR showed the ratio of n-C$_3$F$_7$I to iso-C$_3$F$_7$I to be 95:5. The tube was heated to 80° C. and maintained at that temperature for 26 hours. At that time, $^{19}$F NMR showed the ratio of n-$C_3F_7I$ to iso-$C_3F_7I$ to be 3:97. Complete conversion was achieved after 36 hours at 80° C. Conversion was quantitative; selectivity was over 98%.

Example 7

Isomerization of N-perfluoropropyl Bromide

As in Example 6, using 20 mmol of n-perfluoropropyl bromide (99% pure from PCR Corp.), 1 g of aluminum chlorofluoride and 3 mmol of HFP, after 22 hours at 130° C. according to $^{19}F$ NMR, the reaction mixture contained 10% of perfluoro-isopropyl bromide and 90% of perfluoro-n-propyl bromide. Conversion of starting material was 10%. Selectivity was 100%.

Example 8

Isomerization of n-$C_4F_9Br$

A mixture of 9 g (30 mmol) of n-$C_4F_9Br$, 4,5 g (30 mmol) of HFP and 1 g of ACF was kept at 130° C. for 20 hours. At this point the reaction mixture according to $^{19}F$ NMR contained 2% HFP, 53% of n-$C_4F_9Br$, 27% $CF_3CFBrC_2F_5$, 16% of $(CF_3)_2C=CFC_2F_5$ and 2% of unidentified product. The conversion of the starting bromide was 33%; the selectivity of the isomerization was 100%.

What is claimed is:

1. A process for the isomerization of $R_fCF_2CF_2X'$, wherein $R_f$ is $C_1$ to $C_{12}$ and X' is I or Br, to $R_fCFX'CF_3$, comprising
    contacting $R_fCF_2CF_2X$, with a Lewis acid-based catalytic system, optionally with agitation.
2. The process of claim 1 wherein the Lewis acid catalyst system is aluminum chlorofluoride/fluoroolefin wherein the fluoroolefin is cyclic or linear $C_3$–$C_{12}$.
3. The process of claim 1 wherein the Lewis acid catalyst system is aluminum chlorofluoride/fluoroolefin wherein the fluoroolefin is hexafluoropropene.
4. The process of claim 1 carried out in the presence of a solvent or diluent selected from perfluoroalkanes, perfluoroethers, the cyclic dimer of hexafluoropropene, perfluorodimethylcyclobutanes; perfluoroethers and perfluoro tertiary amines.
5. The process of claim 4 wherein the solvent or diluent is the cyclic dimer of hexafluoropropene.
6. The process of claim 1 carried out at about −10° C. to about 180° C.
7. The process of claim 6 carried out at about 25° C. to 180° C.
8. The process of claim 6 carried out at about 50° C. to 150° C.
9. The process of claim 1 wherein in $R_fCF_2CF_2X'$ $R_f$ is $CF_3$ and X' is I or Br.

* * * * *